(12) United States Patent
Kim et al.

(10) Patent No.: US 9,320,490 B2
(45) Date of Patent: Apr. 26, 2016

(54) ULTRASOUND DIAGNOSTIC APPARATUS AND CONTROL METHOD THEREOF

(75) Inventors: Kang Sik Kim, Seongnam-si (KR); Tai Kyong Song, Seoul (KR); Jin Ho Chang, Seoul (KR); Yang Mo Yoo, Goyang-si (KR); Jae Hee Song, Cheongju-si (KR); Seong Min Jin, Daegu (KR); Choye Kim, Gangneung-si (KR)

(73) Assignees: SAMSUNG ELECTRONICS CO., LTD., Suwon-si (KR); Industry-University Cooperation Foundation Sogang University, Seoul (KR)

( * ) Notice: Subject to any disclaimer, the term of this patent is extended or adjusted under 35 U.S.C. 154(b) by 477 days.

(21) Appl. No.: 13/304,107

(22) Filed: Nov. 23, 2011

(65) Prior Publication Data
US 2012/0136253 A1    May 31, 2012

(30) Foreign Application Priority Data
Nov. 25, 2010  (KR) .................. 10-2010-0117786

(51) Int. Cl.
*A61B 8/14*   (2006.01)
*A61B 8/08*   (2006.01)
(Continued)

(52) U.S. Cl.
CPC .............. *A61B 8/08* (2013.01); *A61B 8/5207* (2013.01); *A61B 8/54* (2013.01); *G01S 7/52033* (2013.01)

(58) Field of Classification Search
CPC ............. A61B 2019/5274; A61B 2019/5272; A61B 8/5207; A61B 8/54; A61B 8/08; G01S 7/52033

USPC .................. 600/437, 443; 382/128; 345/179
See application file for complete search history.

(56) References Cited

U.S. PATENT DOCUMENTS

| 4,433,304 A | * | 2/1984 | Engle | ............................ 330/281 |
| 4,662,380 A |   | 5/1987 | Riley | |
| 6,120,446 A | * | 9/2000 | Ji et al. | ......................... 600/437 |

(Continued)

FOREIGN PATENT DOCUMENTS

KR   10-2007-0054820 A   5/2007

OTHER PUBLICATIONS

Communication dated Apr. 29, 2013, issued by the Korean Intellectual Property Office in counterpart Korean Application No. 10-2010-0117786.

(Continued)

*Primary Examiner* — Long V Le
*Assistant Examiner* — Helene Bor
(74) *Attorney, Agent, or Firm* — Sughrue Mion, PLLC

(57) ABSTRACT

An ultrasound diagnostic apparatus to improve picture quality of images by automatically adjusting image parameters, and a control method thereof are provided. The ultrasound diagnostic apparatus includes an image signal processor to perform envelope detection processing on ultrasound image data, and an image parameter processor to calculate a Time Gain Compensation (TGC) parameter from the envelope detection processed ultrasound image data, adjust the envelope detection processed ultrasound image data based on the TGC parameter, and calculate a Dynamic Range (DR) parameter from the envelope detection processed ultrasound image data adjusted based on the TGC parameter to apply the DR parameter to the envelope detection processed ultrasound image data.

19 Claims, 9 Drawing Sheets

(51) Int. Cl.
*A61B 8/00* (2006.01)
*G01S 7/52* (2006.01)

(56) References Cited

U.S. PATENT DOCUMENTS

| | | | |
|---|---|---|---|
| 6,689,060 B2 | 2/2004 | Phelps et al. | |
| 6,743,174 B2* | 6/2004 | Ng et al. | 600/437 |
| 7,604,594 B2* | 10/2009 | Adams et al. | 600/437 |
| 7,787,680 B2* | 8/2010 | Ahn et al. | 382/128 |
| 2003/0187353 A1 | 10/2003 | Ng et al. | |
| 2007/0165925 A1* | 7/2007 | Ahn et al. | 382/128 |

OTHER PUBLICATIONS

Chinese Office Action dated Sep. 3, 2014 issued by State Intellectual Property Office of the PR of China in counterpart Chinese Patent Application No. 201110394010.4.

* cited by examiner

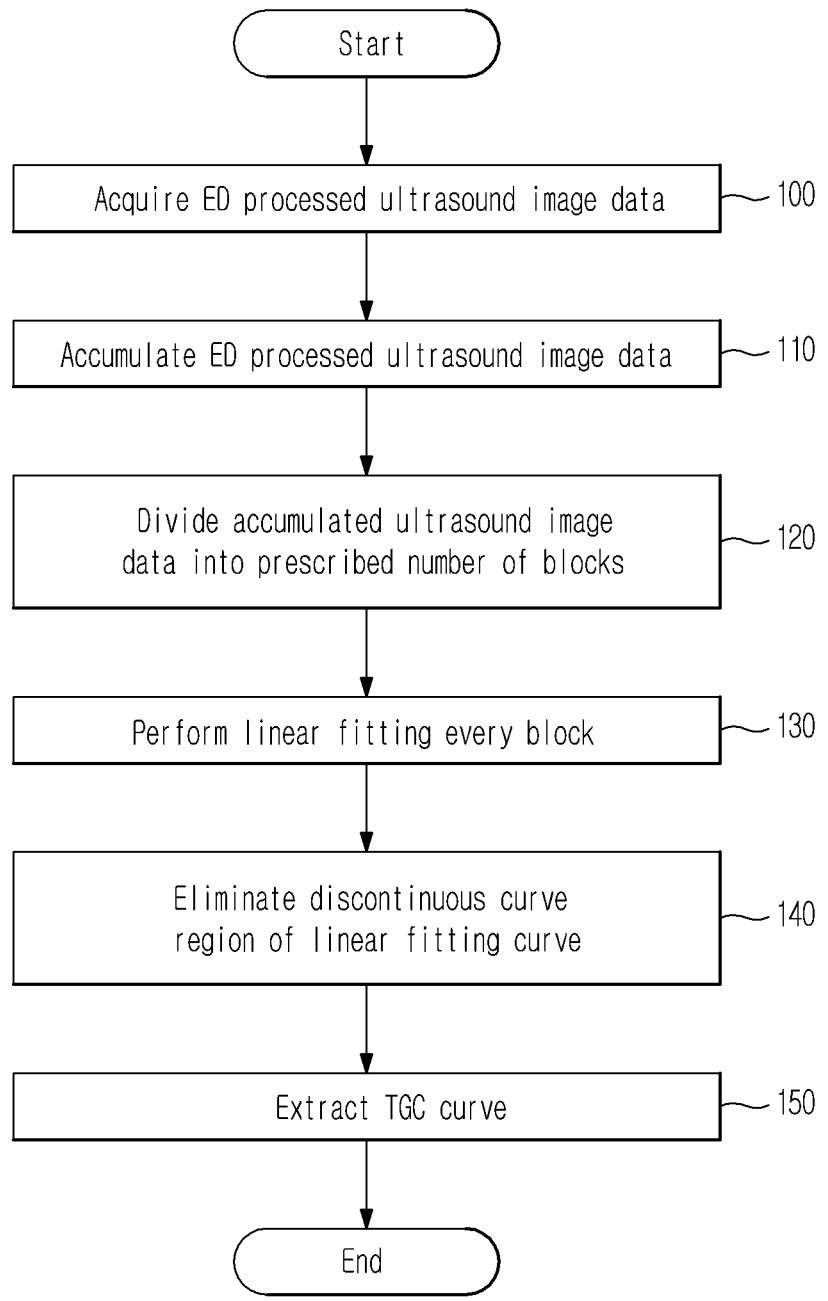

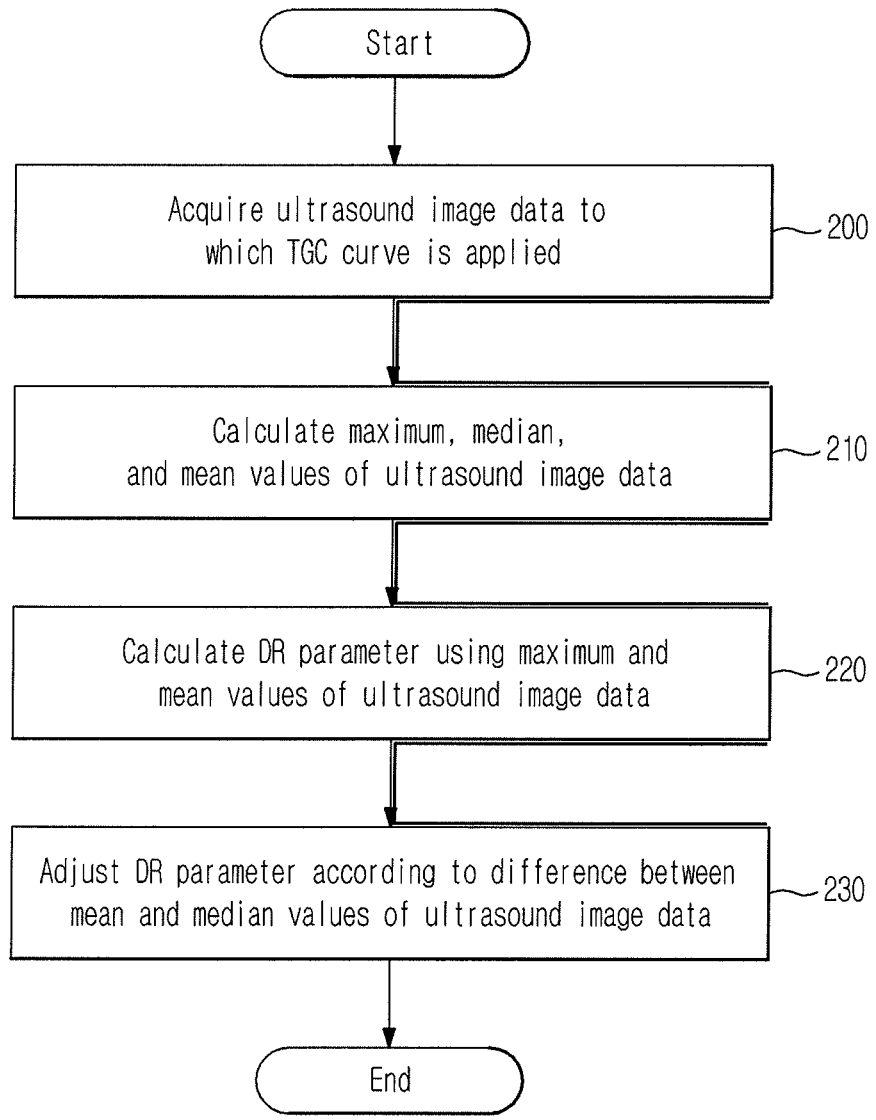

ULTRASOUND DIAGNOSTIC APPARATUS AND CONTROL METHOD THEREOF

CROSS-REFERENCE TO RELATED APPLICATION

This application claims priority from Korean Patent Application No. 10-2010-0117786, filed on Nov. 25, 2010 in the Korean Intellectual Property Office, the disclosure of which is incorporated herein by reference.

BACKGROUND

1. Field

Apparatuses and methods consistent with exemplary embodiments relate to an ultrasound diagnostic apparatus, and a control method thereof.

2. Description of the Related Art

An ultrasound diagnostic apparatus is one of important diagnostic systems which have a wide variety of applications. Especially, ultrasound systems are used extensively in the field of medicine due to the noninvasive and nondestructive nature with respect to an object. Recent high-performance ultrasound systems are used to generate two- or three-dimensional images of the interior of an object.

To observe an object, it is necessary to acquire an optimal ultrasound image which shows the object clearly. To this end, an ultrasound system adjusts image parameters such as gain, Dynamic Range (DR), and Time Gain Compensation (TGC) according to a setting value input by a user to adjust the brightness, resolution, contrast, etc. of an ultrasound image.

In a conventional ultrasound diagnostic apparatus, a user must directly fine-tune image parameters minutely in order to acquire an optimal ultrasound image, thereby causing fatigue and increasing time to acquire an ultrasound image due to a complicated control procedure.

SUMMARY

Exemplary embodiments provide an ultrasound diagnostic apparatus to improve picture quality of images by automatically adjusting image parameters, and a control method thereof.

In accordance with an aspect of an exemplary embodiment, there is provided an ultrasound diagnostic apparatus including an image signal processor to perform envelope detection processing upon ultrasound image data, and an image parameter processor to calculate a Time Gain Compensation (TGC) parameter from the envelope detection processed ultrasound image data, adjust the envelope detection processed ultrasound image data based on the TGC parameter, and calculate a Dynamic Range (DR) parameter from the envelope detection processed ultrasound image data adjusted based on the TGC parameter to apply the DR parameter to the envelope detection processed ultrasound image data.

The image parameter processor may include a TGC processor to calculate the TGC parameter, and the TGC processor may calculate a TGC curve for the envelope detection processed ultrasound image data and apply the TGC curve to the envelope detection processed ultrasound image data.

The TGC processor may calculate the TGC curve for the envelope detection processed ultrasound image data by accumulating the envelope detection processed ultrasound image data, dividing the accumulated envelope detection processed ultrasound image data into a prescribed number of blocks, performing linear fitting with respect to each block, and calculating a curve corresponding to an implicit function of a linear fitting curve derived by performing the linear fitting.

The TGC processor may adjust the linear fitting curve using a mean value of a discontinuous curve region so as to eliminate the discontinuous curve region when the discontinuous curve region is present on the linear fitting curve.

The TGC processor may determine the TGC curve by calculating a curve corresponding to an implicit function of the adjusted linear fitting curve.

The TGC processor may determine that the envelope detection processed ultrasound image data is noise if the envelope detection processed ultrasound image data to which the TGC curve is applied is less than a first reference after applying the TGC curve to the envelope detection processed ultrasound image data.

The TGC processor may lower a size of the envelope detection processed ultrasound image data by dividing the envelope detection processed ultrasound image data judged to be noise by a second reference value when the envelope detection processed ultrasound image data is judged to be noise.

The second reference value may be a TGC curve value multiplied by the envelope detection processed ultrasound image data judged to be noise or an arbitrary value predetermined during design.

The image parameter processor may include a DR processor to calculate a DR parameter, and the DR processor may calculate the DR parameter using a maximum value, a mean value, and a median value of the envelope detection processed ultrasound image data adjusted based on the TGC parameter.

The DR processor may determine a value obtained by subtracting a prescribed value from the maximum value of the envelope detection processed ultrasound image data as a high value and determine a value obtained by subtracting a prescribed value from the mean value of the envelope detection processed ultrasound image data as a low value.

The DR processor may adjust the DR parameter according to a difference between a mean value and a median value of the envelope detection processed ultrasound image data.

The DR processor may adjust the DR parameter by increasing the high value as the difference between the mean value and the median value is increased.

In accordance with an aspect of another exemplary embodiment, there is provided a control method of an ultrasound diagnostic apparatus including performing envelope detection processing upon ultrasound image data, extracting a TGC parameter from the envelope detection processed ultrasound image data, adjusting the envelope detection processed ultrasound image data based on the TGC parameter, and calculating a DR parameter from the envelope detection processed ultrasound image data adjusted based on the TGC parameter to apply the DR parameter to the envelope detection processed ultrasound image data.

The extraction of a TGC parameter may include accumulating the envelope detection processed ultrasound image data, dividing the accumulated envelope detection processed ultrasound image data into a prescribed number of blocks, performing linear fitting with respect to each block, and calculating a TGC curve corresponding to an implicit function of a linear fitting curve derived by performing the linear fitting.

The adjustment of the envelope detection processed ultrasound image data based on the TGC parameter may include applying the TGC curve to the envelope detection processed ultrasound image data.

The control method may further include determining that the envelope detection processed ultrasound image data is noise if the envelope detection processed ultrasound image data to which the TGC curve is applied is less than a first reference value after applying the TGC curve to the envelope detection processed ultrasound image data.

The control method may further include lowering a size of the envelope detection processed ultrasound image data by dividing the envelope detection processed ultrasound image data judged to be noise by a second reference value when the envelope detection processed ultrasound image data is judged to be noise.

The control method may further include adjusting the linear fitting curve using a mean value of a discontinuous curve region so as to eliminate the discontinuous curve region when the discontinuous curve region is present on the linear fitting curve.

The calculation of a DR parameter from the envelope detection processed ultrasound image data may include calculating the DR parameter using a maximum value, a mean value, and a median value of the envelope detection processed ultrasound image data adjusted based on the TGC parameter.

The calculation of a DR parameter may include determining a value obtained by subtracting a prescribed value from the maximum value of the envelope detection processed ultrasound image data as a high value and determining a value obtained by subtracting a prescribed value from the mean value of the envelope detection processed ultrasound image data as a low value.

The control method may further include adjusting the calculated DR parameter according to a difference between a mean value and a median value of the envelope detection processed ultrasound image data.

BRIEF DESCRIPTION OF THE DRAWINGS

These and/or other aspects will become apparent and more readily appreciated from the following description of the exemplary embodiments, taken in conjunction with the accompanying drawings of which:

FIG. 8 is a control flow chart of a TGC curve extracting operation of an image parameter processor of an ultrasound diagnostic apparatus according to an exemplary embodiment; and FIG. 9 is a control flow chart of a DR parameter calculating operation of an image parameter processor of an ultrasound diagnostic apparatus according to an exemplary embodiment.

DETAILED DESCRIPTION

Reference will now be made in detail to the exemplary embodiments, examples of which are illustrated in the accompanying drawings.

Figure 1:
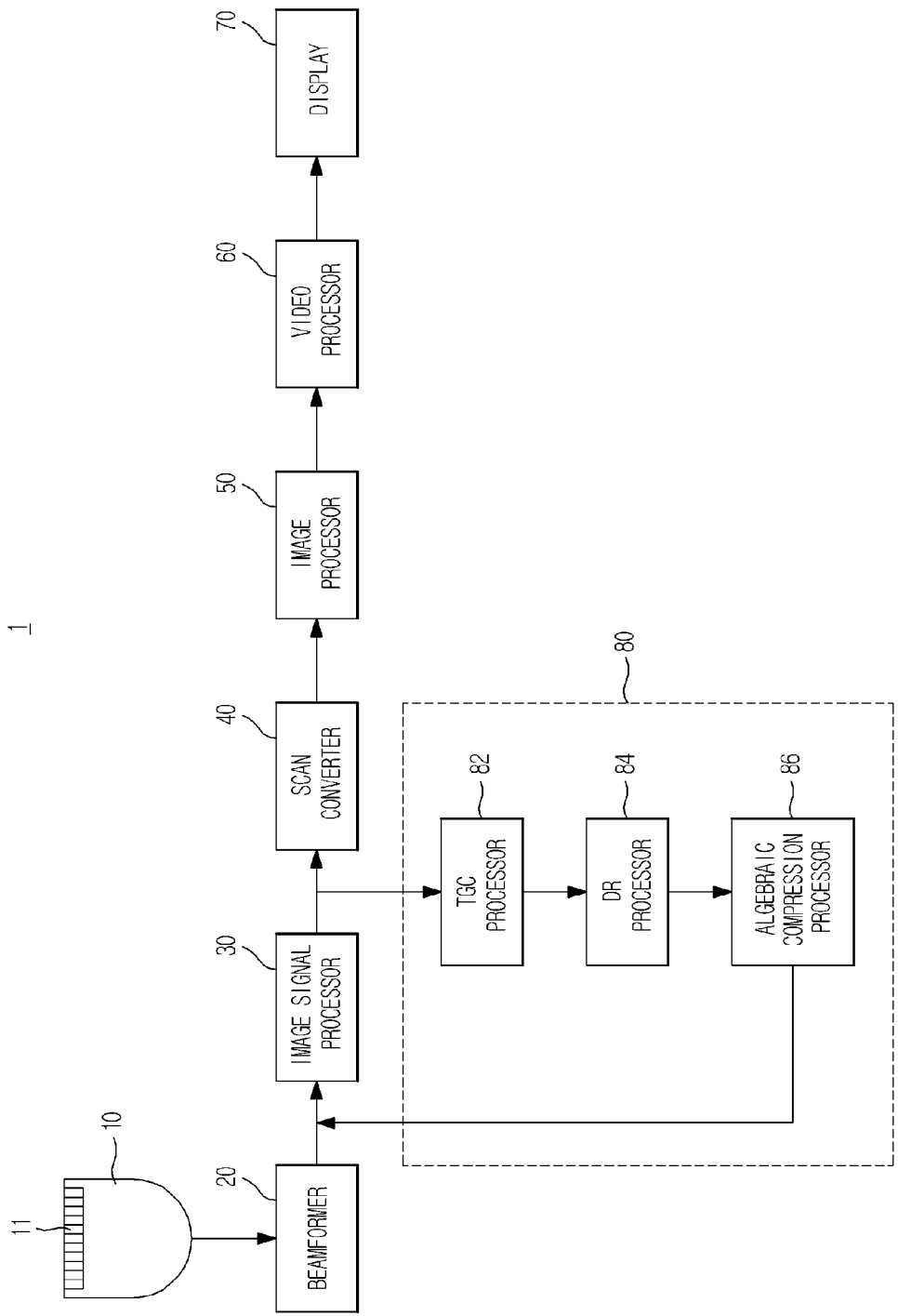
FIG. 1 is a block diagram of an ultrasound diagnostic apparatus according to an exemplary embodiment.

FIG. 1 is a block diagram of an ultrasound diagnostic apparatus according to an exemplary embodiment.

An ultrasound diagnostic apparatus 1 may include a probe 10, a beamformer 20, an image signal processor 30, a scan converter 40, an image processor 50, a video processor 60, a display 70, and an image parameter processor 80. The image signal processor 30, the image processor 50, the video processor 60, and the image parameter processor 80 may be integrated into at least one processor.

The probe 10 may include a plurality of one or two-dimensional transducers 11. The probe 10 appropriately delays input times of pulses input to the respective transducers 11 to transmit a focused ultrasound beam to an object (not shown) along a transmission scan line. Ultrasound echo signals reflected from the object are input to the respective transducers 11 with different reception times and the respective transducers 11 generate the input ultrasound echo signals.

The beamformer 20 focuses the ultrasound echo signals transmitted by the respective transducers 11 of the probe on the object, and adds time delays to the ultrasound echo signals which are reflected from the object and input to the respective transducers 11 to focus the ultrasound echo signals.

The image signal processor 30, for example a digital signal processor (DSP), performs envelope detection processing to detect the size of the ultrasound echo signals based on the ultrasound echo signals focused by the beamformer 20, thereby forming ultrasound image data. That is, the image signal processor 30 forms the ultrasound image data based on location information of a plurality of points on each scan line and data obtained from the respective points. The ultrasound image data includes coordinates on an X-Y coordinate system of each point, angle information of each scan line with respect to a vertical scan line, and data obtained from each point. Performing the envelope detection processing upon a signal is disclosed in detail in U.S. Pat. No. 6,689,060, the disclosure of which is incorporated by reference.

The scan converter 40 scan-converts the ultrasound image data so that the ultrasound image data generated from the image signal processor 30 may be displayed on a display region of the display 70.

The image processor 50 performs various types of image processing, for example B-mode and M-mode Doppler image processing, upon the scan-converted ultrasound image data generated by the scan converter 40 in order to display an ultrasound image in a form desired by a user on the display 70.

The video processor 60 processes the scan-converted ultrasound image data so as to be displayed on the display 70 as an ultrasound image and transmits the processed ultrasound image data to the display 70.

The display 70 displays the ultrasound image data generated from the video processor 60 as an ultrasound image.

The image parameter processor 80 includes a TGC processor 82, a DR processor 84, and an algebraic compression processor 86.

The TGC processor 82 calculates a TGC parameter from the envelope-detection (ED) processed ultrasound image data generated from the image signal processor 30. The function and operation of the TGC processor 82 will be described in detail later with reference to FIG. 3.

The DR processor 84 calculates a DR parameter from the ED processed ultrasound image data to which a TGC curve generated from the TGC processor 82 is applied. The DR parameter refers to an image parameter to adjust the contrast of an ultrasound image. The function and operation of the DR processor 84 will be described in detail later with reference to FIG. 7.

The algebraic compression processor 86 performs algebraic compression using a logarithmic function on the ED processed ultrasound image data. As a value of the DR parameter is increased, the slope of the logarithmic function is increased and thus the contrast of the ED processed ultrasound image data is increased. The algebraic compression processor 86 performs algebraic compression on the ED processed ultrasound image data to which the TGC parameter and the DR parameter are applied.

Figure 2:
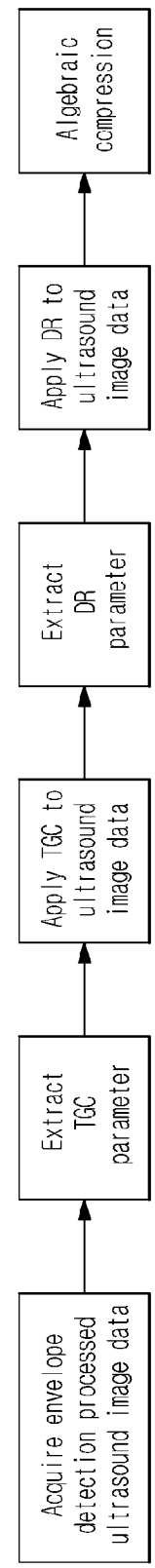
FIG. 2 is a block diagram of an image parameter processor of an ultrasound diagnostic apparatus according to an exemplary embodiment.
Figure 3:
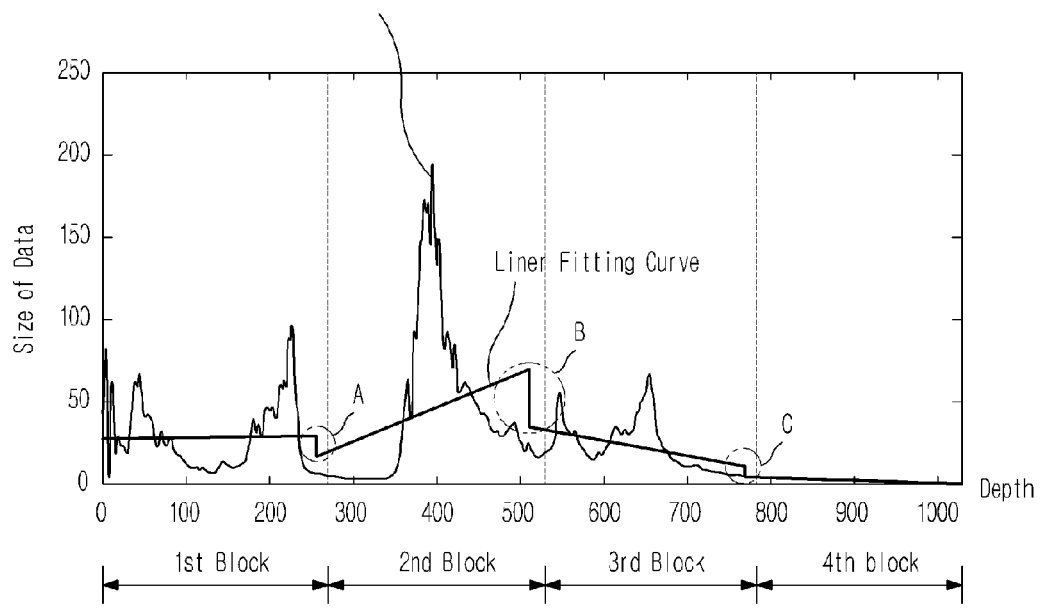
FIG. 3 is a graph to describe a TGC parameter extraction method in an ultrasound diagnostic apparatus according to an exemplary embodiment.
Figure 4:
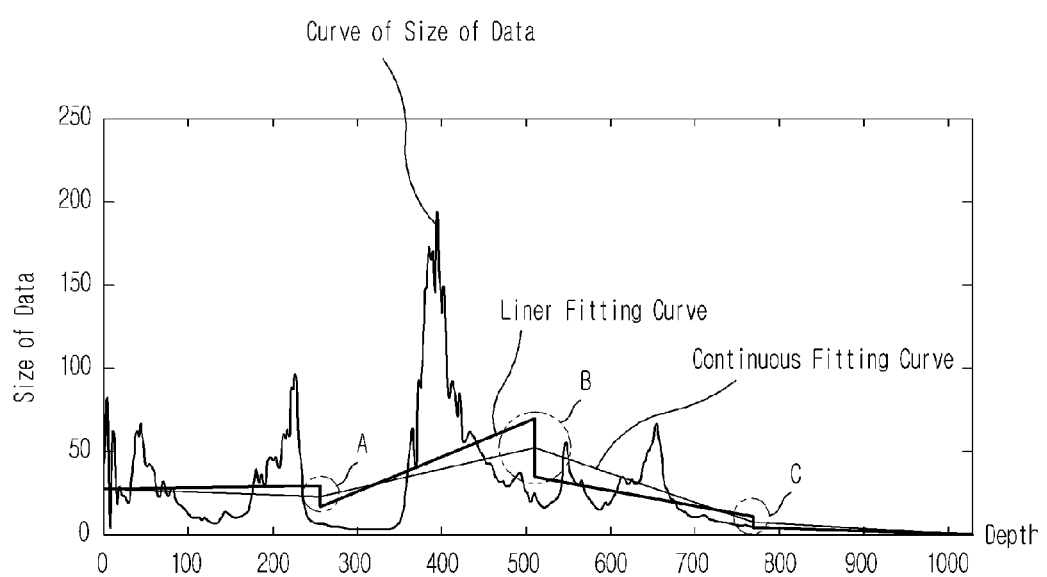
FIG. 4 is a graph to describe a method of eliminating a discontinuous region of a linear fitting curve of the graph of FIG. 3.
Figure 5:
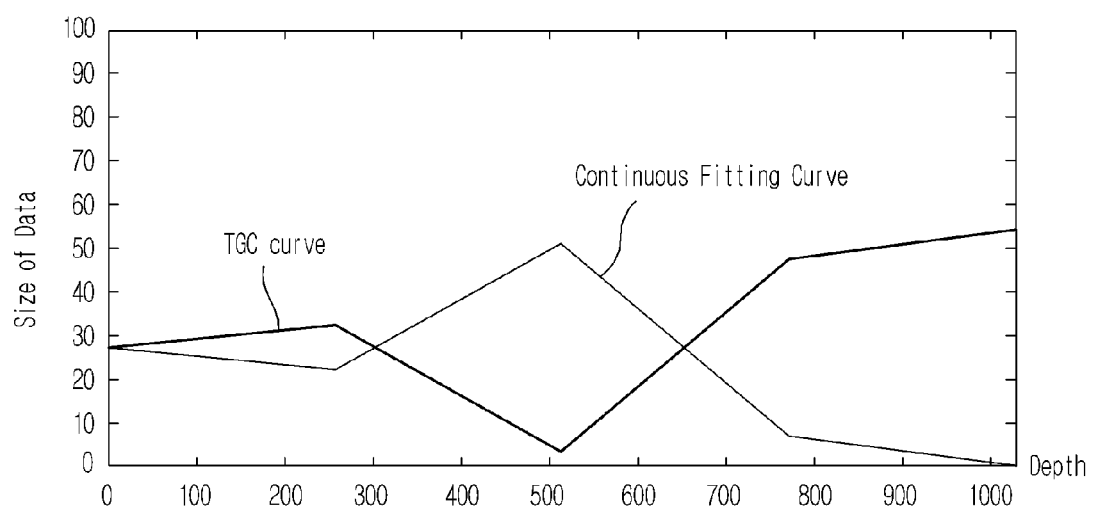
FIG. 5 is a graph illustrating a TGC curve corresponding to an implicit function of a continuous fitting curve shown in the graph of FIG. 4.
Figure 6:
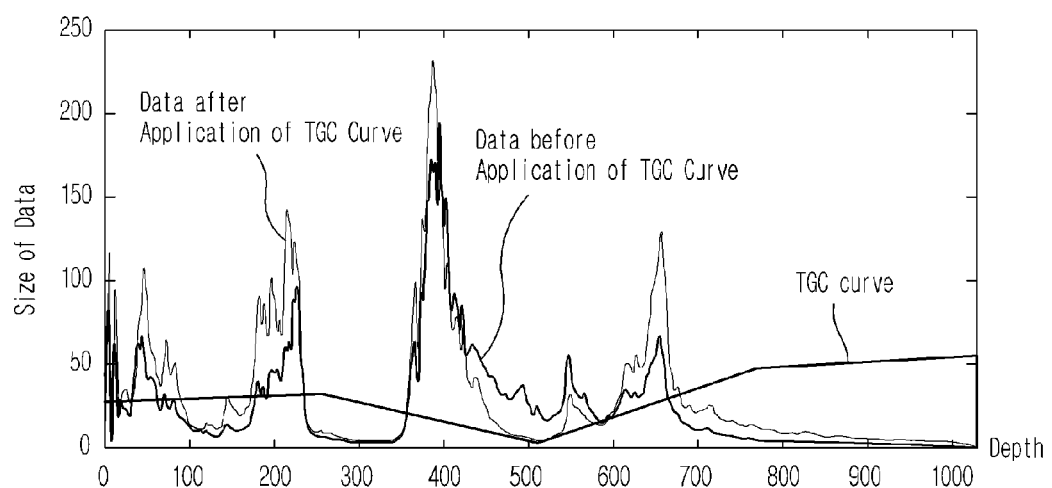
FIG. 6 is a graph illustrating the application of a TGC curve to ultrasound image data.
Figure 7:
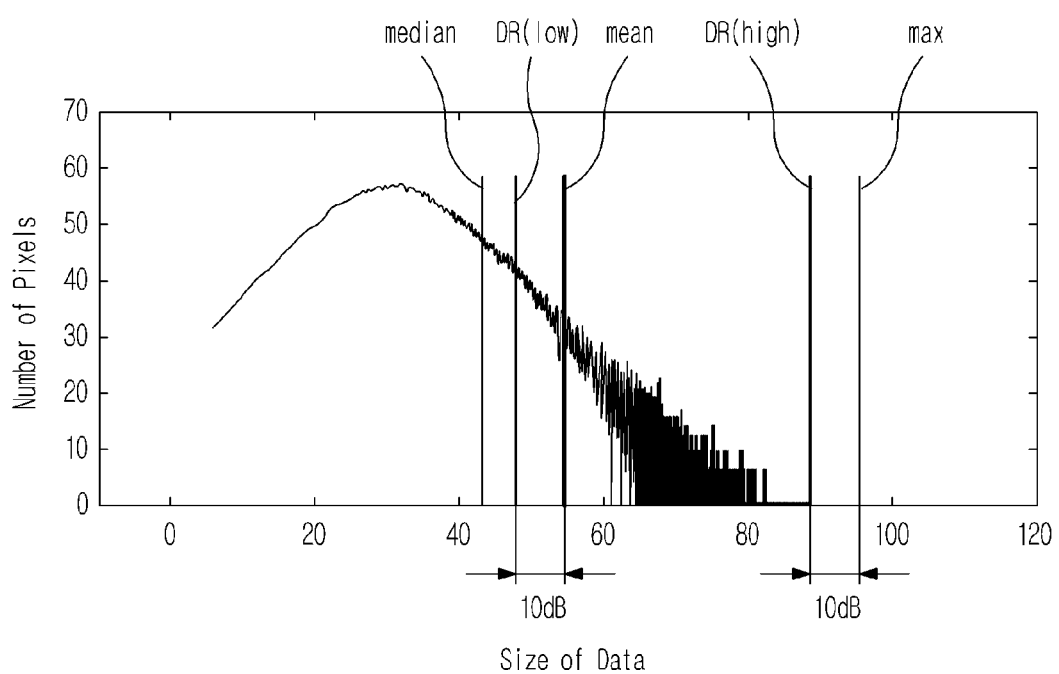
FIG. 7 is a graph to describe a DR parameter extraction method in an ultrasound diagnostic apparatus according to an exemplary embodiment.

FIG. 2 is a block diagram of an image parameter processor of an ultrasound diagnostic apparatus according to an exemplary embodiment, FIG. 3 is a graph to describe a TGC parameter extraction method in an ultrasound diagnostic apparatus according to an exemplary embodiment, FIG. 4 is a graph to describe a method of eliminating a discontinuous region of a linear fitting curve of the graph of FIG. 3, FIG. 5 is a graph illustrating a TGC curve corresponding to an implicit function of a continuous fitting curve shown in the graph of FIG. 4, FIG. 6 is a graph illustrating the application of a TGC curve to ultrasound image data, and FIG. 7 is a graph to describe a DR parameter extraction method in an ultrasound diagnostic apparatus according to an exemplary embodiment.

The image parameter processor 80 calculates a TGC parameter and a DR parameter upon receiving ED processed ultrasound image data from the image signal processor 30, and applies the calculated parameters to the whole frame of the ED processed ultrasound image data.

The TGC processor 82 extracts the TGC parameter from the ED processed ultrasound image data. Hereinafter, a method for the TGC processor 82 to extract the TGC parameter will be described in detail.

Referring to FIG. 3, the TGC processor 82 accumulates the ED processed ultrasound image data in a horizontal direction. Here, the horizontal direction of the ED processed ultrasound image data is perpendicular to the depth direction of the ED processed ultrasound image data. In FIG. 3, the axis of abscissa denotes the depth of the ED processed ultrasound image data and the axis of ordinate denotes the size (that is, amplitude) of the ED processed ultrasound image data located in a horizontal direction at the same depth. The size of ED processed ultrasound image data is proportional to brightness.

The TGC processor 82 divides the accumulated ED processed ultrasound image data into a prescribed number of blocks. In FIG. 3, the accumulated ED processed ultrasound image data is divided into four blocks.

The TGC processor 82 performs linear fitting upon the amplitude of the ED processed ultrasound image data every block so as to recognize a trend in the amplitude of the ED processed ultrasound image data. Linear fitting of the amplitude of ED processed ultrasound image data corresponds to curve fitting of the ED process ultrasound image data. The TGC processor 82 may divide a non-linear curve of an input signal into a plurality of pieces to perform fitting by applying a piecewise linear function every piece and may generate a linear output according to the slope of a non-linear curve of each piece. Curve fitting of a signal is applying a piecewise linear function to the signal so as to recognize a trend in the signal. If the TGC processor 82 performs curve fitting on the ED processed ultrasound image data, a linear fitting curve is generated.

The TGC processor 82 eliminates discontinuous curve regions such as points A, B, and C shown in FIG. 3. The TGC processor 82 uses a mean value of a discontinuous curve region in order to eliminate a discontinuous curve region of a linear fitting curve. The TGC processor 82 adjusts the linear fitting curve using a mean value of a discontinuous curve region (that is, a median value of the amplitude of data) as a connecting point.

Referring to FIG. 4, it will be appreciated that a continuous fitting curve is obtained by connecting median values (or mean values) of the amplitudes of accumulated ED processed ultrasound image data at discontinuous points A, B, and C. Meanwhile, when a fitting curve is discontinuous, extracted ED processed ultrasound image data has a boundary.

Referring to FIG. 5, the TGC processor 82 extracts a TGC curve. The TGC processor 82 extracts a TGC curve corresponding to an implicit function of a continuous fitting curve. When a linear fitting curve calculated in a previous procedure is continuous, the TGC processor 82 extracts a curve corresponding to an implicit function of the linear fitting curve as a TGC curve. When a linear fitting curve calculated in a previous procedure is discontinuous, the TGC processor 82 extracts, as a TGC curve, a curve corresponding to an implicit function of a continuous fitting curve which has corrected the linear fitting curve using the above-described method.

The TGC processor 82 applies a TGC curve to the ED processed ultrasound image data. If the TGC curve is applied to the ED processed ultrasound image data, uniformity of the ED processed ultrasound image data may be increased.

Referring to FIG. 6, it may be appreciated that the amplitude of the ED processed ultrasound image data which is attenuated according to depth may be compensated by the application of the TGC curve to the ED processed ultrasound image data.

After the application of the TGC curve to the ED processed ultrasound image data, if the amplitude of the ED processed ultrasound image data is less than a preset first reference value, the TGC processor 82 determines that the ED processed ultrasound image data is noise. If the ED processed ultrasound image data to which the TGC curve is applied is judged to be noise, the TGC processor 82 lowers the amplitude of the ED processed ultrasound image data by dividing the ED processed ultrasound image data by a TGC value or by a preset second reference value. The preset second reference value is determined in consideration of the first reference value by a designer.

The DR processor 84 sets a DR parameter using the ED processed ultrasound image data to which the TGC curve is applied. Referring to FIG. 7, the DR processor 84 sets a DR parameter using a maximum value, a mean value, and a median value of the ED processed ultrasound image data to which the TGC curve is applied.

The maximum value of the ED processed ultrasound image data to which the TGC curve is applied indicates a value of the ED processed ultrasound image data having the largest pixel value. A mean value of the ED processed ultrasound image data to which the TGC curve is applied indicates a value calculated in consideration of the size of the ED processed ultrasound image data and the number of ED processed ultrasound image data (or pixels) having that size. For example, if the number of the ED processed ultrasound image data having a size of 'a' is 2 and if the number of data having a size of 'b' is 3, then the mean value of data is (a*2+b*3)/(2+3). A median value of the ED processed ultrasound image data to which the TGC curve is applied indicates a value corresponding to the middle of the largest value and the smallest value of the ED processed ultrasound image data. For example, if the largest value of the ED processed ultrasound image data is 100 and if the smallest value of the ED processed ultrasound image data is 0, then a median value of the EC processed ultrasound image data is 50.

As indicated in the following Equation 1, the DR processor 84 may determine, as a high value of a DR parameter, a value obtained by subtracting a prescribed value, for example 10 dB, from the maximum value of the ED processed ultrasound image data to which the TGC curve is applied. The DR processor 84 may determine, as a low value of a DR parameter, a value obtained by subtracting a prescribed value, for example 10 dB, from the mean value of the ED processed ultrasound image data to which the TGC curve is applied.

$$DR\_high\_offset = max - 10 \text{ dB:high value}$$

$$DR\_low\_offset = mean - 10 \text{ dB:low value} \quad \text{[Equation 1]}$$

The DR processor 84 may correct a DR parameter considering the difference between the mean value of the ED processed ultrasound image data to which the TGC curve is applied and the median value of the ED processed ultrasound image data to which the TGC curve is applied.

The DR processor 84 determines that the bigger the difference between the mean value of the ED processed ultrasound image data to which the TGC curve is applied and the median value of the ED processed ultrasound image data to which the TGC curve is applied is, the more information of the ED processed ultrasound image data having a larger size includes. Accordingly, the DR processor 84 varies a DR parameter by increasing a high value of a DR determined by Equation 1. A varied degree of the high value of the DR is preset according to the difference between a mean value and a median value of data. For instance, if the difference between a mean value and a median value of data is 20 dB, a high value may be increased by 5 dB and if the difference therebetween is 30 dB, a high value may be increased by 8 dB.

FIG. 8 is a control flow chart to describe a TGC curve extracting operation of an image parameter processor of an ultrasound diagnostic apparatus according to an exemplary embodiment.

The TGC processor 82 acquires ED processed ultrasound image data from the image signal processor 30 in step 100. The ED processed ultrasound image data may also be called an envelope signal.

The TGC processor 82 accumulates the ED processed ultrasound image data in a horizontal direction in step 110. Namely, the TGC processor 82 accumulates a mean size of the ED processed ultrasound image data by detecting pixels existing at the same depth at each region of the ED processed ultrasound image data.

Next, the TGC processor 82 divides the accumulated ED processed ultrasound image data into a prescribed number of blocks in step 120.

The TGC processor 82 performs linear fitting upon the amplitude of data every block in step 130. Linear fitting of the amplitude of the ED processed ultrasound image data is applying a piecewise linear function to a signal so as to recognize a trend in the signal. If the TGC processor 82 performs the linear fitting upon the ED processed ultrasound image data, a linear fitting curve is generated.

The TGC processor 82 eliminates a discontinuous curve region of the linear fitting curve in step 140. To eliminate the discontinuous curve region of the linear fitting curve, the TGC processor 82 uses a mean value of the discontinuous curve region. The TGC processor 82 corrects the linear fitting curve using a mean value of the discontinuous curve region (that is, a median value of the size of data) as a connecting point.

The TGC processor 82 extracts a TGC curve corresponding to an implicit function of the linear fitting curve in step 150.

FIG. 9 is a control flow chart to describe a DR parameter calculating operation of an image parameter processor of an ultrasound diagnostic apparatus according to an exemplary embodiment.

The DR processor 84 acquires the ED processed ultrasound image data to which a TGC curve is applied from the TGC processor 82 in step 200.

The DR processor 84 calculates a maximum value, a mean value, and a median value of the ED processed ultrasound image data to which the TGC curve is applied in step 210.

The DR processor 84 determines, as a high value of a DR parameter, a value obtained by subtracting a prescribed value from the maximum value of the ED processed ultrasound image data to which the TGC curve is applied and determines, as a low value of the DR parameter, a value obtained by subtracting a prescribed value from the mean value of the ED processed ultrasound image data to which the TGC curve is applied in step 220.

The DR processor 84 adjusts the DR parameter by increasing a high value of a DR determined according to the difference between the mean value of the ED processed ultrasound image data to which the TGC curve is applied and the median value of the ED processed ultrasound image data to which the TGC curve is applied in step 230.

According to an aspect of an exemplary embodiment, since image parameters may be automatically adjusted, a user may diagnose ultrasound images more accurately and conveniently.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:

1. An ultrasound diagnostic apparatus comprising:
   a probe including a plurality of transducers which are configured to obtain ultrasound image data;
   an image signal processor configured to perform envelope detection processing on the ultrasound image data; and
   an image parameter processor configured to calculate a Time Gain Compensation (TGC) parameter from the envelope detection processed ultrasound image data, to adjust the envelope detection processed ultrasound image data based on the TGC parameter, and to calculate a Dynamic Range (DR) parameter from the adjusted envelope detection processed ultrasound image data to apply the DR parameter to the adjusted envelope detection processed ultrasound image data,
   wherein the image parameter processor comprises a TGC processor configured to extract the TGC parameter by calculating a TGC curve for the envelope detection processed ultrasound image data, and to adjust the envelope detection processed ultrasound image data based on the TGC parameter by applying the TGC curve to the envelope detection processed ultrasound image data, and
   wherein the TGC processor is further configured to determine that the envelope detection processed ultrasound image data is noise if the envelope detection processed ultrasound image data to which the TGC curve is applied is less than a first reference value after applying the TGC curve to the envelope detection processed ultrasound image data.

2. The ultrasound diagnostic apparatus according to claim 1, wherein the TGC processor is further configured to calculate the TGC curve for the envelope detection processed ultrasound image data by accumulating the envelope detection processed ultrasound image data, dividing the accumulated envelope detection processed ultrasound image data into a prescribed number of blocks, performing linear fitting with respect to each block, and calculating a curve corresponding to an implicit function of a linear fitting curve derived by performing the linear fitting.

3. The ultrasound diagnostic apparatus according to claim 2, wherein the TGC processor is further configured to adjust the linear fitting curve using a mean value of a discontinuous curve region so as to eliminate the discontinuous curve region when the discontinuous curve region is present on the linear fitting curve.

4. The ultrasound diagnostic apparatus according to claim 3, wherein the TGC processor is further configured to calculate the TGC curve by calculating a curve corresponding to an implicit function of the adjusted linear fitting curve.

5. The ultrasound diagnostic apparatus according to claim 1, wherein the TGC processor is further configured to lower a size of the envelope detection processed ultrasound image data by dividing the envelope detection processed ultrasound image data judged to be noise by a second reference value when the envelope detection processed ultrasound image data is judged to be noise.

6. The ultrasound diagnostic apparatus according to claim 5, wherein the second reference value is a TGC curve value multiplied by the envelope detection processed ultrasound image data judged to be noise or an arbitrary value.

7. The ultrasound diagnostic apparatus according to claim 1, wherein the image parameter processor comprises a DR processor configured to calculate a DR parameter by calculating the DR parameter using a maximum value, a mean value, and a median value of the adjusted envelope detection processed ultrasound image data.

8. The ultrasound diagnostic apparatus according to claim 7, wherein the DR processor is further configured to determine a value obtained by subtracting a prescribed value from the maximum value of the adjusted envelope detection processed ultrasound image data as a high value of the DR parameter, and to determine a value obtained by subtracting a prescribed value from the mean value of the adjusted envelope detection processed ultrasound image data as a low value of the DR parameter.

9. The ultrasound diagnostic apparatus according to claim 8, wherein the DR processor is further configured to determine the DR parameter according to a difference between a mean value and a median value of the envelope detection processed ultrasound image data.

10. The ultrasound diagnostic apparatus according to claim 9, wherein the DR processor is further configured to adjust the DR parameter by increasing the high value of the DR parameter as the difference between the mean value of the envelope detection processed ultrasound image and the median value of the envelope detection processed ultrasound image is increased.

11. A control method of an ultrasound diagnostic apparatus comprising a probe, comprising:
obtaining, by the probe, ultrasound image data;
performing, by the ultrasound diagnostic apparatus, envelope detection processing on the ultrasound image data;
extracting, by the ultrasound diagnostic apparatus, a Time Gain Compensation (TGC) parameter from the envelope detection processed ultrasound image data;
adjusting, by the ultrasound diagnostic apparatus, the envelope detection processed ultrasound image data based on the TGC parameter; and
calculating, by the ultrasound diagnostic apparatus, a Dynamic Range (DR) parameter from the adjusted envelope detection processed ultrasound image data to apply the DR parameter to the envelope detection processed ultrasound image data,
wherein the extracting the TGC parameter comprises calculating, by the ultrasound diagnostic apparatus, a TGC curve for the envelope detection processed ultrasound image data,
wherein the adjusting comprises applying, by the ultrasound diagnostic apparatus, the TGC curve to the envelope detection processed ultrasound image data, and
wherein the method further comprises determining, by the ultrasound diagnostic apparatus, that the envelope detection processed ultrasound image data is noise if the envelope detection processed ultrasound image data to which the TGC curve is applied is less than a first reference value after applying the TGC curve to the envelope detection processed ultrasound image data.

12. The control method according to claim 11, wherein the extracting, by the ultrasound diagnostic apparatus, the TGC parameter comprises accumulating, by the ultrasound diagnostic apparatus, the envelope detection processed ultrasound image data, dividing, by the ultrasound diagnostic apparatus, the accumulated envelope detection processed ultrasound image data into a prescribed number of blocks, performing, by the ultrasound diagnostic apparatus, linear fitting with respect to each block, and calculating, by the ultrasound diagnostic apparatus, the TGC curve corresponding to an implicit function of a linear fitting curve derived by performing the linear fitting.

13. The control method according to claim 11, further comprising lowering, by the ultrasound diagnostic apparatus, a size of the envelope detection processed ultrasound image data by dividing the envelope detection processed ultrasound image data judged to be noise by a second reference value when the envelope detection processed ultrasound image data is judged to be noise.

14. The control method according to claim 12, further comprising adjusting, by the ultrasound diagnostic apparatus, the linear fitting curve using a mean value of a discontinuous curve region so as to eliminate the discontinuous curve region when the discontinuous curve region is present on the linear fitting curve.

15. The control method according to claim 11, wherein the calculating, by the ultrasound diagnostic apparatus, the DR parameter from the adjusted envelope detection processed ultrasound image data comprises calculating the DR parameter using a maximum value, a mean value, and a median value of the adjusted envelope detection processed ultrasound image data.

16. The control method according to claim 15, wherein the calculating the DR parameter comprises determining, by the ultrasound diagnostic apparatus, a value obtained by subtracting a prescribed value from the maximum value of the adjusted envelope detection processed ultrasound image data as a high value and determining, by the ultrasound diagnostic apparatus, a value obtained by subtracting a prescribed value from the mean value of the adjusted envelope detection processed ultrasound image data as a low value.

17. The control method according to claim 16, further comprising adjusting the calculated DR parameter according to a difference between a mean value and a median value of the envelope detection processed ultrasound image data.

18. An ultrasound diagnostic apparatus comprising:
a probe including a plurality of transducers which are configured to generate ultrasound echo signals;

an image signal processor configured to perform envelope detection to detect a size of the ultrasound echo signals forming ultrasound image data;

an image parameter processor configured to calculate a Time Gain Compensation (TGC) parameter from the ultrasound image data formed by the image signal processor, to calculate an image parameter to adjust contrast of the ultrasound image, and to apply the calculated image parameter to the ultrasound image data, wherein the image parameter processor comprises a TGC processor configured to calculate the TGC parameter by calculating a TGC curve for the ultrasound image data and applying the TGC curve to the ultrasound image data, and wherein the TGC processor is further configured to determine that the ultrasound image data is noise if the ultrasound image data to which the TGC curve is applied is less than a first reference value after applying the TGC curve to the ultrasound image data.

19. An ultrasound diagnostic apparatus comprising:

a probe including a plurality of transducers which are configured to obtain ultrasound image data;

an image signal processor configured to perform envelope detection processing on the ultrasound image data; and an image parameter processor configured to calculate a Time Gain Compensation (TGC) parameter from the envelope detection processed ultrasound image data, to adjust the envelope detection processed ultrasound image data based on the TGC parameter, and to calculate a Dynamic Range (DR) parameter from the adjusted envelope detection processed ultrasound image data to apply the DR parameter to the adjusted envelope detection processed ultrasound image data, wherein the image parameter processor comprises a DR processor configured to calculate a DR parameter, wherein the DR processor is further configured to determine a value obtained by subtracting a prescribed value from the maximum value of the adjusted envelope detection processed ultrasound image data as a high value of the DR parameter, to determine a value obtained by subtracting a prescribed value from the mean value of the adjusted envelope detection processed ultrasound image data as a low value of the DR parameter, and to adjust the DR parameter according to a difference between a mean value and a median value of the envelope detection processed ultrasound image data.

* * * * *